US009280636B2

(12) United States Patent
Raggousis (10) Patent No.: US 9,280,636 B2
(45) Date of Patent: Mar. 8, 2016

(54) ELECTRONIC MEDICAL RECORD DISTRIBUTION, SYSTEMS AND METHODS

(75) Inventor: Konstantinos Raggousis, Horsham, PA (US)

(73) Assignee: QSI Management, LLC, Irvine, CA (US)

(*) Notice: Subject to any disclaimer, the term of this patent is extended or adjusted under 35 U.S.C. 154(b) by 570 days.

(21) Appl. No.: 13/085,046

(22) Filed: Apr. 12, 2011

(65) Prior Publication Data

US 2011/0282688 A1    Nov. 17, 2011

Related U.S. Application Data

(60) Provisional application No. 61/334,259, filed on May 13, 2010.

(51) Int. Cl.
*G06Q 50/22* (2012.01)
*G06F 19/00* (2011.01)
*G06Q 50/24* (2012.01)

(52) U.S. Cl.
CPC .............. *G06F 19/322* (2013.01); *G06Q 50/24* (2013.01)

(58) Field of Classification Search
USPC .......................................................... 705/2–4
See application file for complete search history.

(56) References Cited

U.S. PATENT DOCUMENTS

| 5,915,240 | A | 6/1999 | Karpf | |
|---|---|---|---|---|
| 6,283,761 | B1 * | 9/2001 | Joao | G06F 19/322 128/923 |
| 7,034,691 | B1 * | 4/2006 | Rapaport | G06Q 50/22 340/539.1 |
| 7,181,017 | B1 | 2/2007 | Nagel et al. | |
| 7,630,986 | B1 | 12/2009 | Herz et al. | |
| 7,660,902 | B2 | 2/2010 | Graham et al. | |
| 2002/0010679 | A1 * | 1/2002 | Felsher | 705/51 |
| 2002/0046346 | A1 * | 4/2002 | Evans | 713/200 |
| 2002/0128871 | A1 * | 9/2002 | Adamson | G06F 17/30545 705/3 |
| 2002/0169638 | A1 * | 11/2002 | Rodriguez-Cue | 705/3 |
| 2003/0154110 | A1 * | 8/2003 | Walter | G06F 19/322 705/3 |
| 2004/0024879 | A1 * | 2/2004 | Dingman et al. | 709/227 |
| 2007/0016450 | A1 | 1/2007 | Bhora et al. | |
| 2007/0061393 | A1 | 3/2007 | Moore | |
| 2007/0136378 | A1 | 6/2007 | Karpf et al. | |
| 2008/0004904 | A1 * | 1/2008 | Tran | 705/2 |
| 2008/0021741 | A1 * | 1/2008 | Holla et al. | 705/3 |
| 2008/0249386 | A1 | 10/2008 | Besterman et al. | |
| 2008/0300922 | A1 * | 12/2008 | Forgue et al. | 705/3 |
| 2008/0306872 | A1 * | 12/2008 | Felsher | 705/51 |
| 2011/0113062 | A1 * | 5/2011 | Quinlan | G06F 17/30427 707/770 |
| 2012/0065995 | A1 * | 3/2012 | Singh et al. | 705/3 |

* cited by examiner

*Primary Examiner* — Michael Tomaszewski
(74) *Attorney, Agent, or Firm* — Fish & Tsang, LLP (57) ABSTRACT

Systems and methods for distributing Electronic Medical Records (EMR) from a private practice to authorized mobile devices are presented. EMR data can be exchanged from a private practice with a remote mobile device via an intermediary mobile access service. The service can include one or more servers that tunnel EMR data between the mobile devices and the practice, where a relay server located at the service communicates via an a priori instantiated persistent session with a relay client installed at the practice. The persistent session can be maintained by the relay client thus reducing the burden on the practice to configure or change local network infrastructure.

7 Claims, 9 Drawing Sheets

ELECTRONIC MEDICAL RECORD DISTRIBUTION, SYSTEMS AND METHODS

This application claims priority to U.S. provisional application having Ser. No. 61/334,259 filed on May 13, 2010. This and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is data record distribution technologies.

BACKGROUND

Healthcare providers and practices have an ever increasing need for accessing medical records to ensure they have the latest information or have access to information at a moments notice. Mobile communication devices continue to grow in computational power and allow a healthcare provider to access information from nearly anywhere on Earth. Unfortunately, use of a mobile device to access medical records, especially within a small healthcare practice environment, is fraught with problems.

Figure 1:
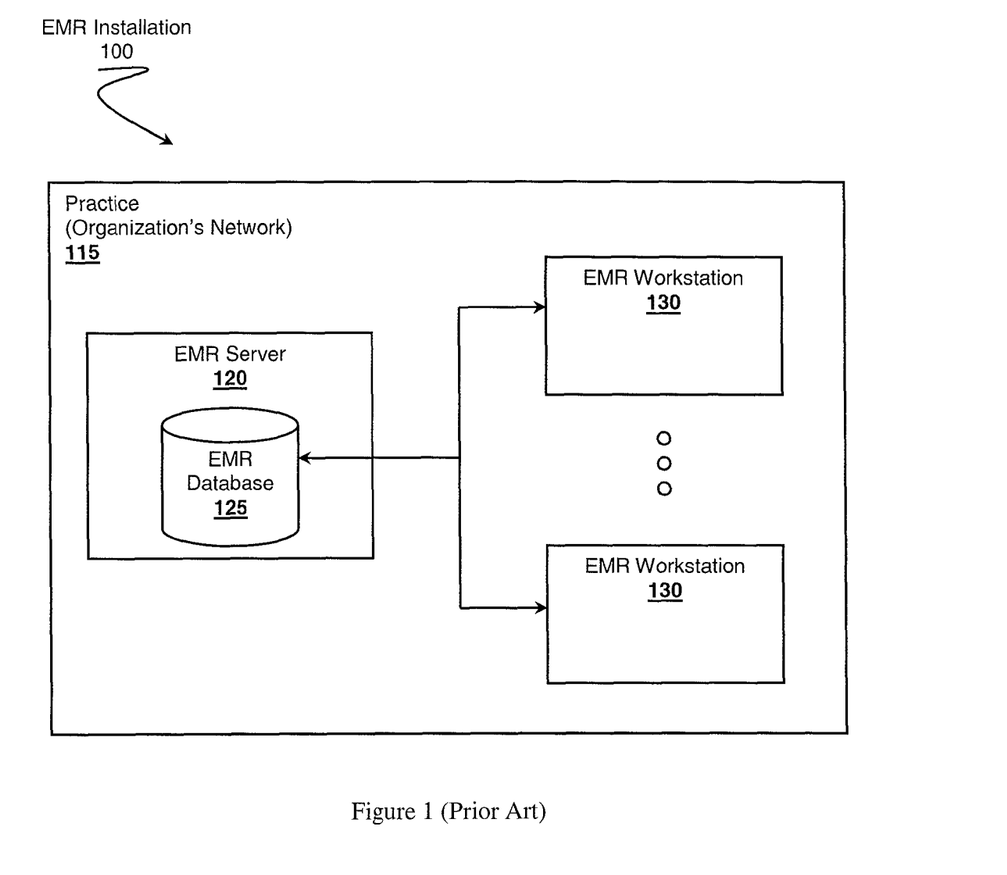
FIG. 1 is a schematic overview of a typical prior art EMR installation.

FIG. 1 presents a typical non-mobile environment associated with a healthcare practice. The practice creates an Electronic Medical Record (EMR) installation 100 by purchasing and installing an EMR server 120 on a local area network within practice 115. EMR server 120 provides access to EMR database 125 storing the practice's medical records, which are often private records or stored in a proprietary format. Members of the practical typically access the records via one or more EMR workstations 130. EMR installation 100 lacks support for allowing mobile communication devices to gain access to EMR database 120.

Others have put forth effort toward providing access to medical records as described in the following references.

U.S. Pat. No. 5,915,240 to Karpf et al. titled "Computer System and Method for Accessing Medical Information over a Network", filed Jun. 12, 1997, describes a system for accessing medical records very similar to the network depicted in FIG. 1.

U.S. Pat. No. 7,034,691 to Rapaport et al. titled "Adaptive Communication Methods and Systems for Facilitating the Gathering, Distribution, and Delivery of Information Related to Medical Care", filed Jan. 25, 2002, describes a medical information distribution system where urgent information can be sent to a person that is highly mobile via a mobile phone.

U.S. Pat. No. 7,181,017 to Nagel et al. titled "System and Method for Secure Three-Party Communications", filed Mar. 25, 2002, contemplates a system where information, including private medical records, can be sent through a third party via secured communication channels.

U.S. Pat. No. 7,630,986 to Herz et al. titled "Secure Data Interchange", filed Oct. 27, 2000, also describes a system where data can be sent through a secured intermediate party and where queries can persist at a server until data arrives satisfying the query.

Although the above references provide useful insights into infrastructural techniques, they fail to address a number of issues that a private practice, or other non-technical data provider, encounters when attempting to provide data to a remote mobile device. One issue includes installation and maintenance of servers, firewalls, routers, software applications, or other highly complex technologies. Individuals in or members of a private practice typically lack technical skills to address managing these or other technologies. In addition, the private practice might lack sufficient funds to outsource such activities to those individuals who do have the required technical skills to deploy such complex technology. Yet another issue that must be addressed by the private practice is integration of mobile devices into their distribution system in a manner that is robust, secured, or seamless without requiring additional effort by individuals at the practice.

U.S. patent application publication 2003/0154110 to Walter et al. titled "Method and Apparatus for Wireless Access to a Health Care Information System", filed Nov. 20, 2002, makes some progress by providing for a wireless handheld device having a persistent connection with a health care information system.

The above references fail to address the technical issues encountered by a practice when creating a viable EMR distribution installation that allows mobile devices to access an EMR database. Ideally a practice could install an EMR distribution system local to their organization where the installed system would automatically instantiate necessary communication infrastructure to support mobile access to locally stored medical records. A more desirable EMR system would not require the practice to manage web servers, firewalls, keep logs, separate mobile content, or other items while still being able to offer remote mobile devices access to private medical records.

Thus, there is still a need for electronic record distribution systems and methods.

SUMMARY OF THE INVENTION

The inventive subject matter provides apparatus, systems and methods in which a remote healthcare worker can use a mobile communications device (e.g., a cell phone, PDA, etc.) to access Electronic Medical Records (EMR) stored on a private EMR database. One aspect of the inventive subject matter includes an EMR distribution system having an EMR relay server that provides a communication bridge between a mobile request device and a healthcare practice where medical records are stored on an EMR database. In some embodiments, the healthcare practice has an EMR relay client that exchanges EMR request data between the EMR relay server and the EMR database. In a preferred embodiment, the EMR relay client automatically establishes a persistent session with the EMR relay server and maintains the session. When mobile devices seek access, they can first communicate with the relay server. As a mobile request device generates EMR requests, the EMR relay server forwards the request through the EMR relay client, which in turn can obtain a result set and send the result set back to the mobile device via the EMR relay server. One should appreciate by automatically establishing a persistent session, possibly in the form of a pending request to the EMR relay server, the healthcare practice is able to establish and maintain remote access to their medical records without requiring technical skills or maintaining complex technologies as discussed further below. The EMR relay server can provide security, logging, monitoring, reporting, alerts, or other management overhead activities associated with allowing mobile devices to gain access to the medical records that would ordinarily be required of the practice.

Other aspects of the inventive subject matter can also include methods of providing access to EMR databases, which include establishing a persistent session between an EMR relay client local to a practice and an EMR relay service hosted by a remote third party. The persistent session can comprise one or more data channels. Each data channel could be a separate connection between the relay client and the relay server, or each channel could be a logical channel constructed within a single connection. Regardless of the channel construction, the session remains persistent. Should connectivity be lost, the EMR relay client can seek to automatically reestablish the session. In some embodiments, the persistent session can take the form of the EMR client establishing a pending request for an EMR access command from the EMR relay service. When the EMR request is received at the EMR client in response to establishing a pending request, the EMR client can send an EMR result set to the mobile requesting device where the EMR result set is consider to be responsive the EMR request. The EMR client can then reestablish the pending request.

The inventive subject matter is also considered to include a more general purpose electronic record distribution system beyond medical records. In some embodiments, the distribution system can also include a channel manager configured to manage one or more channels over a persistent session between a relay client and a remote relay server. One or more communication channels can be configured based on information related to the owner of requested records, the record requestor, or licensing information.

Various objects, features, aspects and advantages of the inventive subject matter will become more apparent from the following detailed description of preferred embodiments, along with the accompanying drawing figures in which like numerals represent like components.

DETAILED DESCRIPTION

It should be noted that while the following description is drawn to a computer/server based Electronic Record (ER) management service, especially an Electronic Medical Record (EMR) management service, various alternative configurations are also deemed suitable and may employ various computing devices including servers, interfaces, systems, databases, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus or services. In especially preferred embodiments, the various services, servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

One should appreciate that the disclosed techniques provide many advantageous technical effects including reducing barriers for gaining access to authorized EMR data without compromising the confidentiality of the data. Furthermore, one should appreciate that the disclosed EMR systems manage the EMR distribution network to allow remote healthcare worker to access seamlessly their medical records without incurring undue burden on a healthcare worker, provider, or practice.

Figure 2:
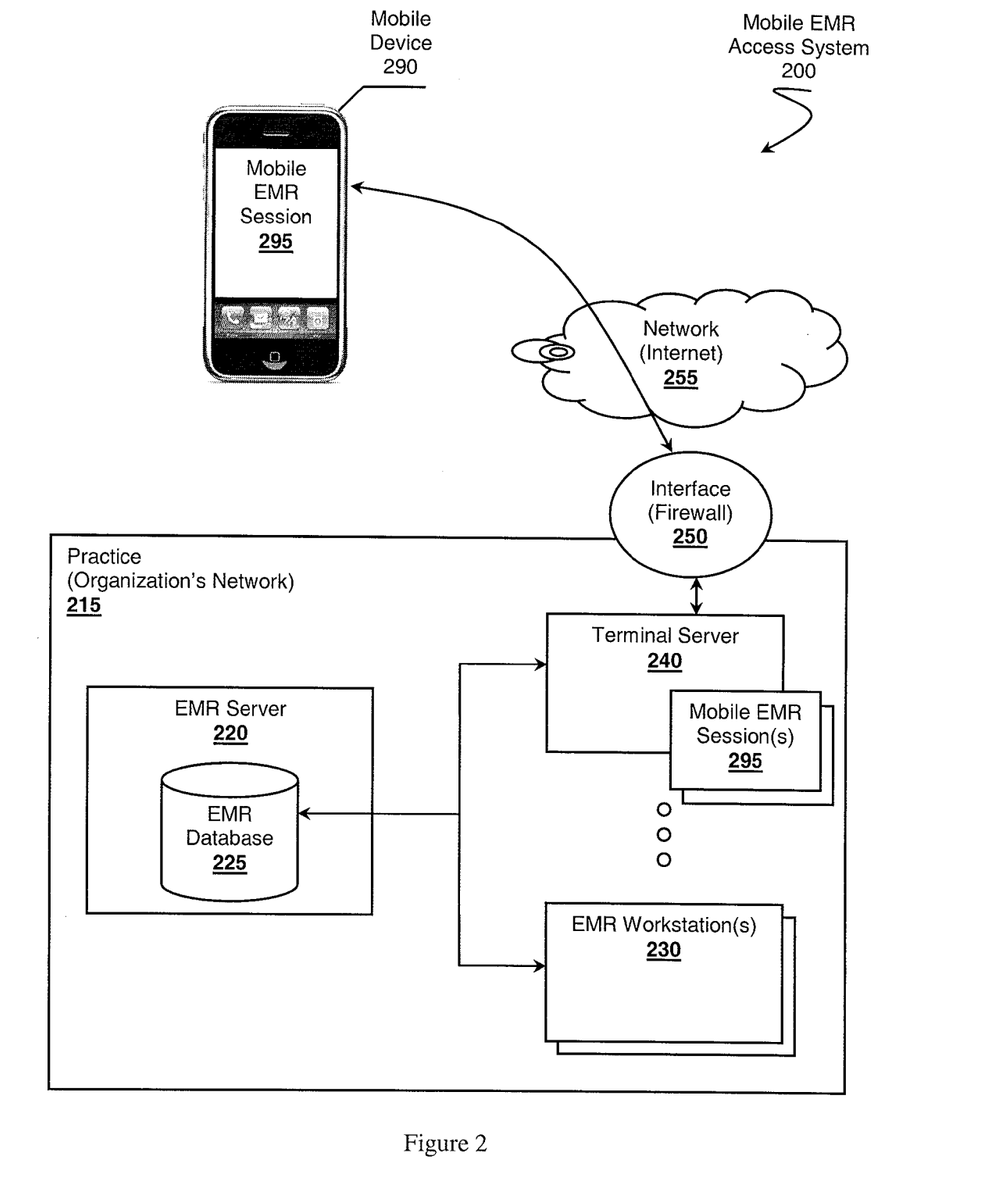
FIG. 2 presents a possible embodiment of an EMR access system, which provides access via a terminal server.

FIG. 2 present a possible approach for providing mobile EMR access system 200 where mobile device 290 (e.g., cell phone, PDA, etc.) can gain access to confidential data stored EMR database 225. In the example shown, terminal server 240 is configured to operate as a remote desktop for mobile device 290. Thus terminal server 240 mimics another EMR workstation 230 from the perspective of EMR server 220, while terminal server 240 manages one or more mobile EMR sessions 295 with mobile device 290. Terminal server 240 can render an image of an executing EMR application and package the image or other EMR data for delivery to mobile device 290. Naturally, practice 215 would likely open one or more appropriate ports on firewall 250 to allow mobile device 290 to exchange data with terminal server 240. The ports of firewall 250 likely remain open to allow terminal server 240 to receive inbound connections at any time.

Although the network interface for practice 215 is presented as firewall 250, other types of network interfaces could also be leveraged or used to allow access to network 255. Other example network interfaces include web services APIs, gateways, routers, switches, cellular interfaces, or other types of network interfaces. One should appreciate that the term "firewall" is used euphemistically to represent a network interface.

An embodiment based on terminal server 240 as several advantages. First, terminal server technology is readily available. Second, terminal server 240, which can be a fully featured computing device, has sufficient computing resources available to interact with EMR server 220 and to execute an EMR workstation application, where the mobile device might not have such resources or might represent a difficult platform on which to deploy a custom EMR application. Third, terminal server 240 allows for rapid migration of existing solutions as described in FIG. 1 from practice-bound deployments to mobile-accessible environments, thus breaking a legacy boundary of practice 115.

The approach outlined in FIG. 2 allows for remote mobile access to EMR data while reducing dependency on technical capabilities within practice 115. Terminal server 240 and firewalls are readily available to practice 115. Still, practice 115 would require some technical expertise to manage terminal server 240 or configure firewall 250 properly.

Figure 3:
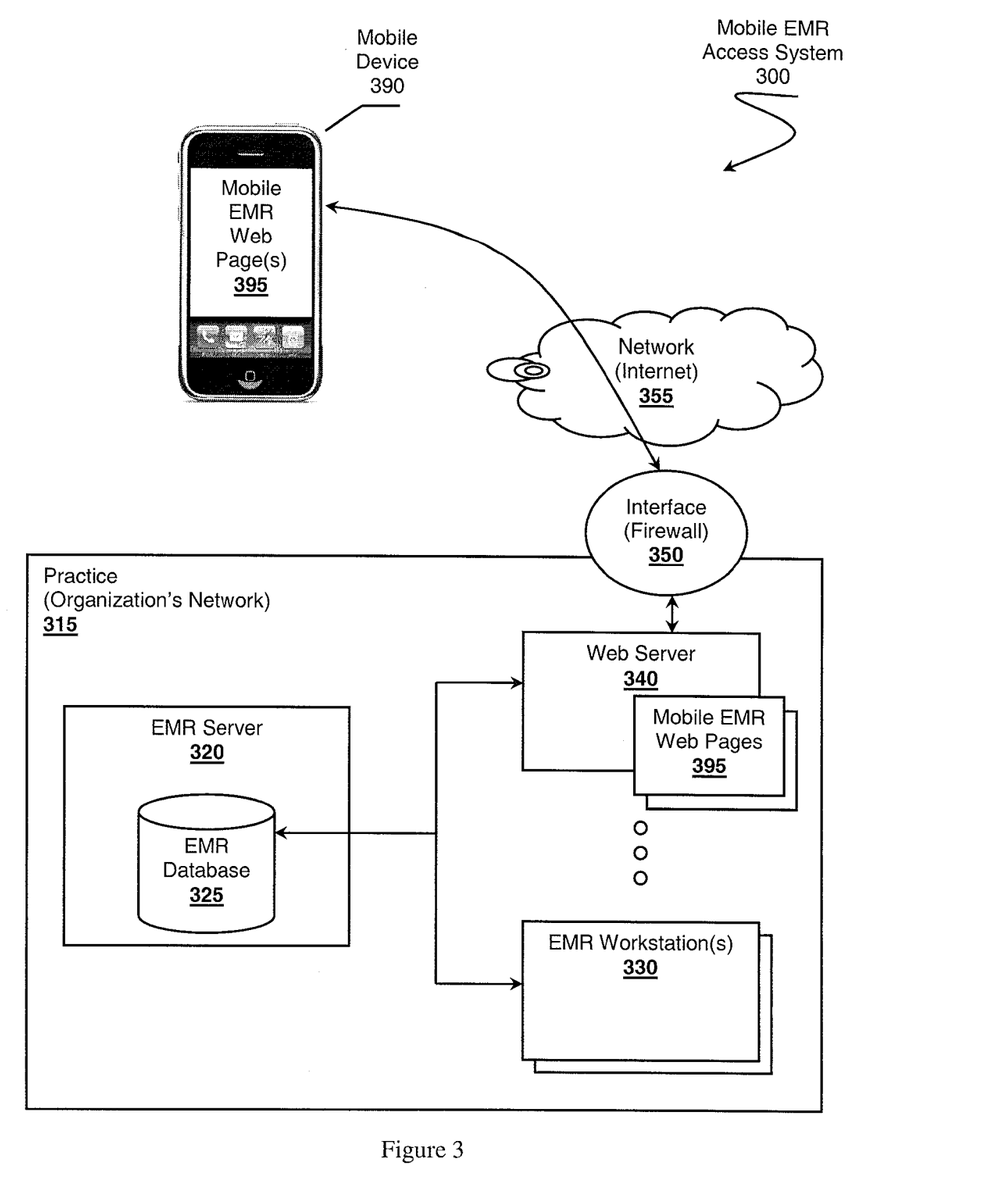
FIG. 3 presents another possible embodiment of an EMR access system, which provides access via a web server.

In FIG. 3, further progress can be made toward reducing installation and maintenance burden. Mobile EMR access system 300 has many similarities with the system illustrated in FIG. 2, with the notable exception that access system 300 comprises web server 340 as opposed to a terminal server. In this example, mobile device 390 is web-enabled with a browser application capable of accessing and displaying mobile EMR web pages 395 over network 355. Mobile device 390 can access web server 340, which is configured with an EMR application similar to those running on EMR workstations 330 and capable of sending queries to EMR server 320. In response to a query EMR server 320 can consult EMR database 325 to provide one or more result sets back to web server 340 for packaging as web pages 395. Such an approach is considered to reduce the burden for configuration on practice 315 because firewall 350 is typically configured by default to allow incoming web-based communications. For example, firewall 350 by default might have TCP ports 80 or 443 open in support for HTTP or HTTPS, respectively. Thus practice 315 would not be required to modify settings of firewall 350. It is also likely that practice 315 would already have web server 340 deployed. Still, practice 315 would be required to install appropriate EMR applications within web server 340 and might be required to configure web server 340 appropriate. Furthermore, practice 315 would have to configure web server 340 with registration information from one or more of mobile device 390. Management of mobile device 390 registration information can include adding devices, removing devices, changing registration information, tracking devices, providing infrastructure to support different types of mobile device 390, or other taking other actions that support mobile device 390.

Figure 4:
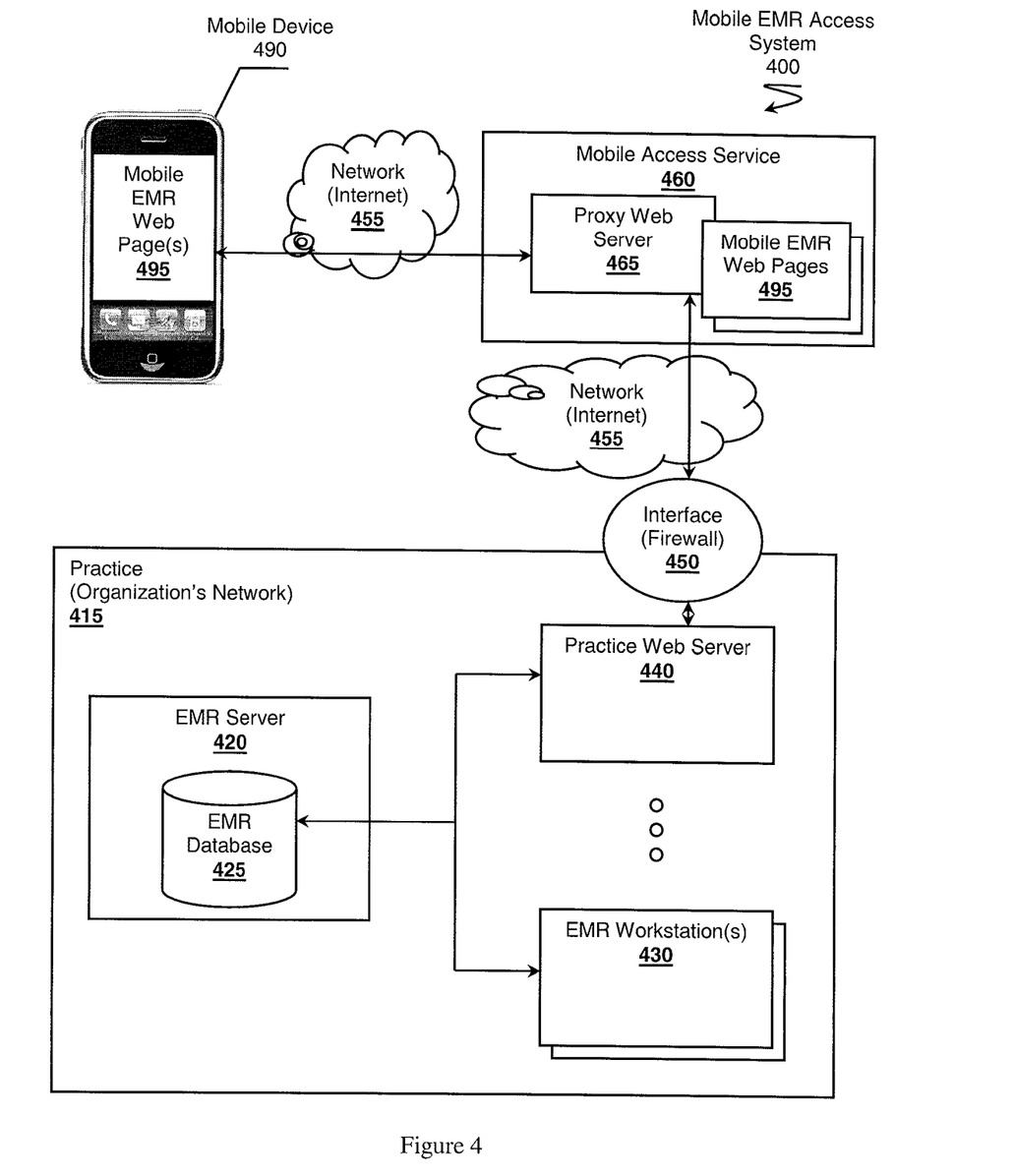
FIG. 4 presents yet another possible embodiment of an EMR access system, which provides access via a mobile access service.

In FIG. 4, mobile EMR access system 400 illustrates yet another more preferred embodiment where the burden of configuring EMR applications is reduced even further. Mobile EMR access system 400 introduces mobile access service 460, which can include proxy web server 465. Rather than requiring practice 415 to register mobile device 490 locally, mobile access service 460 can manage device registration information. When mobile device 490 requests EMR data, mobile device 490 can communication with proxy web server 465 over network 455. Proxy web server 465 can then validate, authenticate, or otherwise verify the registration information of mobile device 490 without comprising the confidentiality of EMR data located in EMR database 425 or without risking exposing practice 415 to unnecessary security risks. Once any suitable or required authentication or authorization steps have been performed, proxy web server 465 can, by proxy, communicate with practice web server 440 to submit queries to EMR server 420.

Web pages 495 can be hosted by practice web server 440 or, more preferably by proxy web server 465. By hosting web pages 495 at mobile access service 460, practice 415 is no longer required to maintain or manage content for each type of mobile device 490. Thus, the EMR applications running on practice web server 440 can be greatly streamlined. In some embodiments, practice web server 440 can offer a secured web services API through which proxy web server 465 can submit requests. As in FIG. 3, firewall 450 does not require any further modification other than to ensure that proxy web server 465 can communicate with practice web server 440.

One should appreciate that mobile access service 460 can operate as a for-fee service in exchange for providing mobile access to practice 415. In some embodiments, mobile access service 460 is preferably operated or managed by the same entity that provide software for EMR server 420, EMR database 425, EMR workstations 430, or even EMR modules that can be installed on web server 440. One advantage to the approach disclosed in FIG. 4 is mobile access service 460 takes responsibility of exchanging information with different types of mobile device 490 according to each device's capability rather than requiring practice 415 to install numerous modules for each type of supported mobile device 490. Still, the practice must maintain one or more open ports to allow the service's web server to establish inbound connections with the practice's web server.

Figure 5:
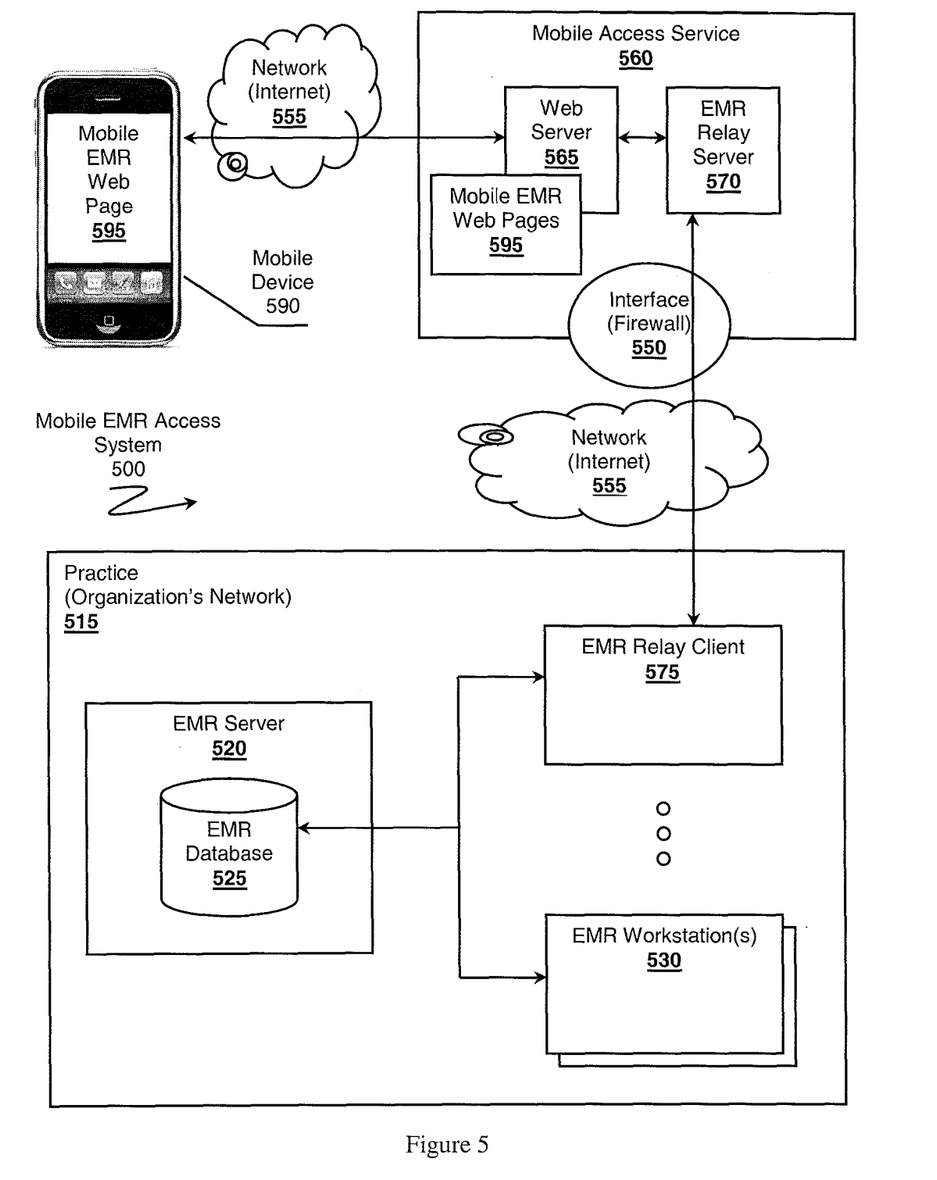
FIG. 5 presents still another possible embodiment of an EMR access system, which provides access via a mobile access service having an EMR relay server.

FIG. 5 illustrates an even more advantageous and preferable approach as represented by mobile EMR access 500. Mobile devices 590 can access EMR records over network 555, which can include any combination of Internet or wireless networks (e.g., cellular networks) Rather than requiring practice 515 to update or configure a web server or network interface (e.g., firewall) appropriately, mobile access service 560 and practice 515 can communicate via an EMR request relay server 570 and an EMR relay client 575, respectively. In such an embodiment, relay server 570 and relay client 575 can establish and maintain a persistent session between practice 515 and mobile access service 560, through which requests for EMR data can be tunneled in a transparent fashion with respect to practice 515. By establishing a persistent session between relay client 575 and relay server 570, practice 515 no longer has to manage its own network interface to ensure connectivity can be achieved in secured fashion.

In a preferred embodiment, relay client 575 establishes the persistent session as an outbound connection from practice 515 to relay server 570 over network 555. An outbound connection avoids requiring practice 515 to alter its existing network interface to allow for incoming connections (e.g., open ports within a firewall), which could increase vulnerability to external security risks. Mobile access service 560 might include firewall 550, which can be easily configured by the entity operating the service to allow incoming connections from practice 515. Once the persistent session has been established, relay server 570 can exchange EMR requests as an intermediary between mobile device 590 and its target practice 515.

A persistent session can take on many forms. In some embodiments, the persistent session can be at least one TCP/IP connection established from relay client 575 to relay server 570. One should appreciate that a single TCP/IP connection could comprise multiple data channels tunneled over the single connection. It is also contemplated, that a session could comprises multiple connections, each of which could be a separate data channel. The persistent session could include management channels, data channels, or other types of channels.

Although the persistent session preferably comprises a transport layer connection, it is also contemplated that the persistent session could be constructed at other layers within a communication stack. The persistent session could be constructed at an application layer, presentation layer, session layer, network layer, link layer, physical layer, or combinations of layers. It is also contemplated that a persistent session could be constructed as a Virtual Private Network between EMR relay client 575 and EMR relay server 570.

Preferably, at least one connection within a persistent session is maintained in an open, connected state, through which relay server 570 is able to initiate a data exchange with relay client 575. For example, upon installation of relay client 575 at practice 515, possibly on EMR server 520, relay client 575 could automatically establish a management channel with relay server 570 that remains open at all times. When the management channel is opened by relay client 575, it could take the form of a pending request for commands from relay server 570. More specifically, relay client 575 notifies relay server 570 that relay client 575 is ready receive requests or queries for locally stored EMR data.

Relay client 575 can simply wait for an EMR request, or other command or remote procedure call, to arrive from relay server 570. Relay client 575 can execute the command upon reception from relay server 570. If relay client 575 suffers a loss of connectivity with relay server 570 then relay client 575 can attempt to reestablish the connection with relay server 570 to ensure the session remains persistent. Status of the persistent session's connectivity can be checked through various methods including polling, heart beats, probes, or other non-invasive techniques.

Although preferred approaches for maintaining a persistent session focus on relay client 575 taking action, it is also contemplated that relay server 570 could attempt to initiate the persistent session. Action by relay client 575 is more preferred because establishing an outgoing network connection from behind a network interface infrastructure is considered to be less burdensome for practice 515 than permitting an incoming connection through the network interface infrastructure.

Mobile device 590 preferably interfaces with mobile access service 560 over network 555 through a web-based communication. As discussed previously, use of a web-based communication can be achieved through a browse application installed on mobile device 590 so that mobile device 590 can render one or more EMR web pages 595 representing an EMR web interface. Upon directing mobile device 590 to web server 565, mobile device 590 can be authenticated or authorized based on stored registration information. Web server 565 can prepare an EMR web interface by presenting web pages 595 to mobile device. As user can make EMR requests through appropriately configured web pages 595 where the web interface can generated the actual EMR request. In some embodiments, mobile device 590 can directly generated the EMR request. When web server 565 receives a request, web server 565 communicates with relay server 570 to package an EMR request targeting practice 515.

The advantages of FIG. 5's configuration should be fully appreciated. A persistent outbound session from practice 515 that is automatically established by relay client 575 eliminates a need for practice 515 to configure their local network interfaces or web servers to allow inbound connections, especially inbound connections from one or more of mobile device 590. Furthermore, use of relay client 575 eliminates the need for practice 515 to modify their own web server with new application modules or packages that provide support for various types of mobile device 590. One should note connections from relay client 575 to relay server 570 can pass through a firewall without trouble, especially when the firewall is enabled with a NAT router. Installation of relay client 575 would be no more egregious than installing EMR server 520, EMR database 525, or EMR workstations 530, well within the skill set of those within the practice. From a networking perspective, relay client 575 can operate as any other networking application.

Figure 6:
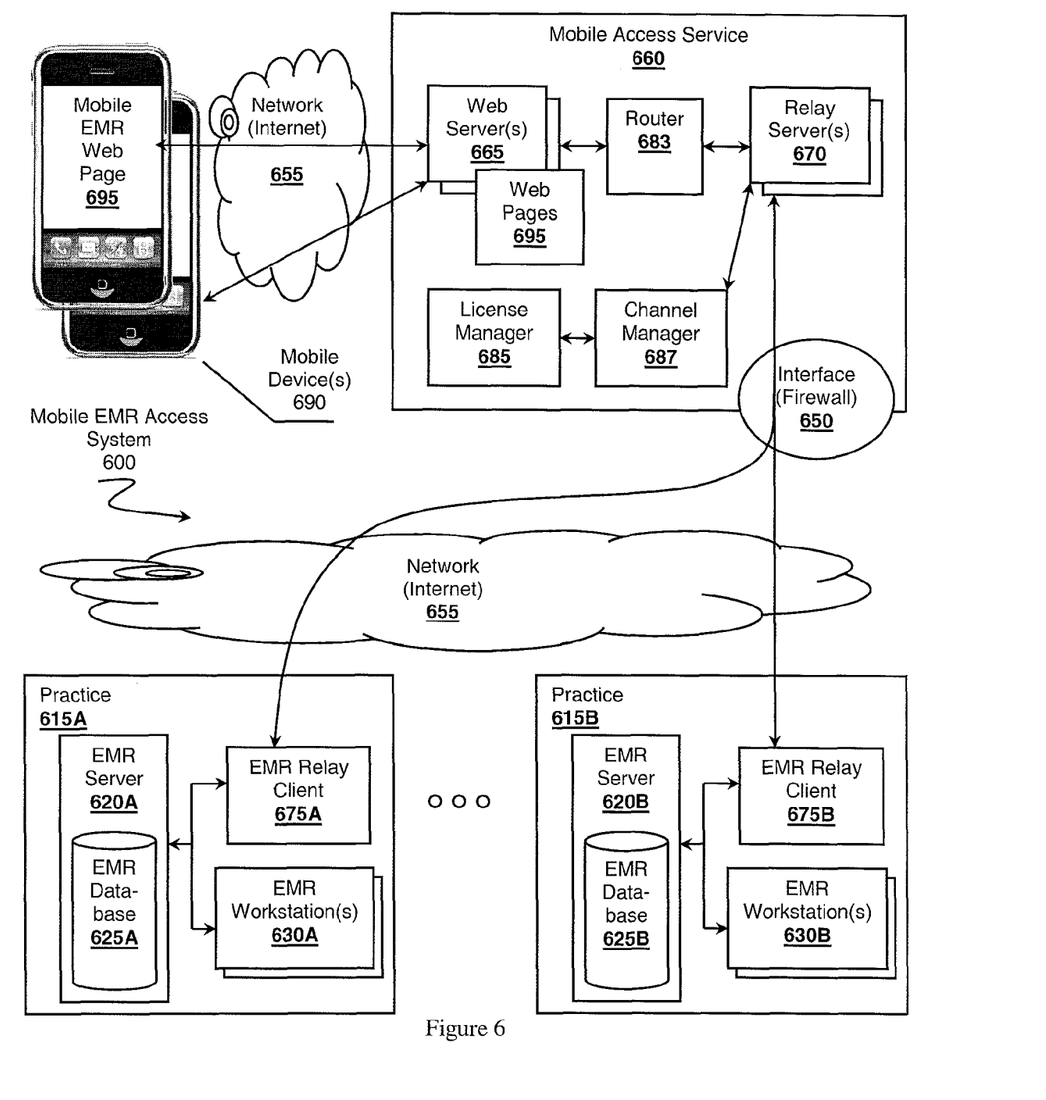
FIG. 6 presents a variation on FIG. 5 where an EMR mobile access service supports multiple private practices.

FIG. 6 expands on the configuration of FIG. 5 by preferably providing support for one or more independent, possibly unaffiliated, practices 615A through 615B. Practices 615A and 615B comprise relay clients 675A and 675B, respectively, capable of communicating with one or more relay servers 670 of mobile access service 660 over network 655. In some embodiments, each relay client 675A or 675B could have a corresponding relay server 670 (e.g., a virtual relay server). It is also contemplated that a single relay server 670 could be configured to support multiple relay clients 675A and 675B, where the single relay server 670 takes on additional responsibilities of properly routing mobile EMR sessions to proper relay clients 675A or 675B. Relay clients 675A and 675B can provide access to EMR servers 620A and 620B respectively in a similar fashion as their respective EMR workstations 630A and 630B. EMR requests from mobile devices 690 can be submitted to EMR databases 625A or 625B to obtain one or more result sets.

The configuration shown in FIG. 6 can also include router 683, license manager 685, or channel manager 687. Router 683 supports routing EMR request information from one or more mobile devices 690 to a proper relay server 670 or a proper channel within a persistent session assigned to target practice 615A or 615B. Routing can be directed according to routing rules based on an authentication token provided by mobile device 690. License manager 685 enforces one or more licenses associated with installed EMR applications and ensures mobile devices 690 are properly authorized to gain access to mobile access service 660 or each of practice's 675A or 675B records stored their respective EMR databases 625A or 625B respectively. Channel manager 687 can manage one or more channels, as desired, over each of practice's 675A or 675B persistent sessions based on licensing information, profile information, practice site information, routing information, or other parameters available to mobile access service 660.

In some embodiments, channel manager 687 manages multiple channels within the persistent session. For example, channels can be created, removed, disabled, enables, or otherwise modified based on various information obtained from mobile device 690 or stored a profile, licensing, site, routing database as discussed below. Channel manager 687 can alter a channels behavior based on whether the mobile device user is an owner of an EMR record, a requester from the practice, or based on license information (e.g., permissions, access levels, etc.). In some embodiment, a patient could use mobile device 690 to access their own records on EMR database 625A.

Figure 7:
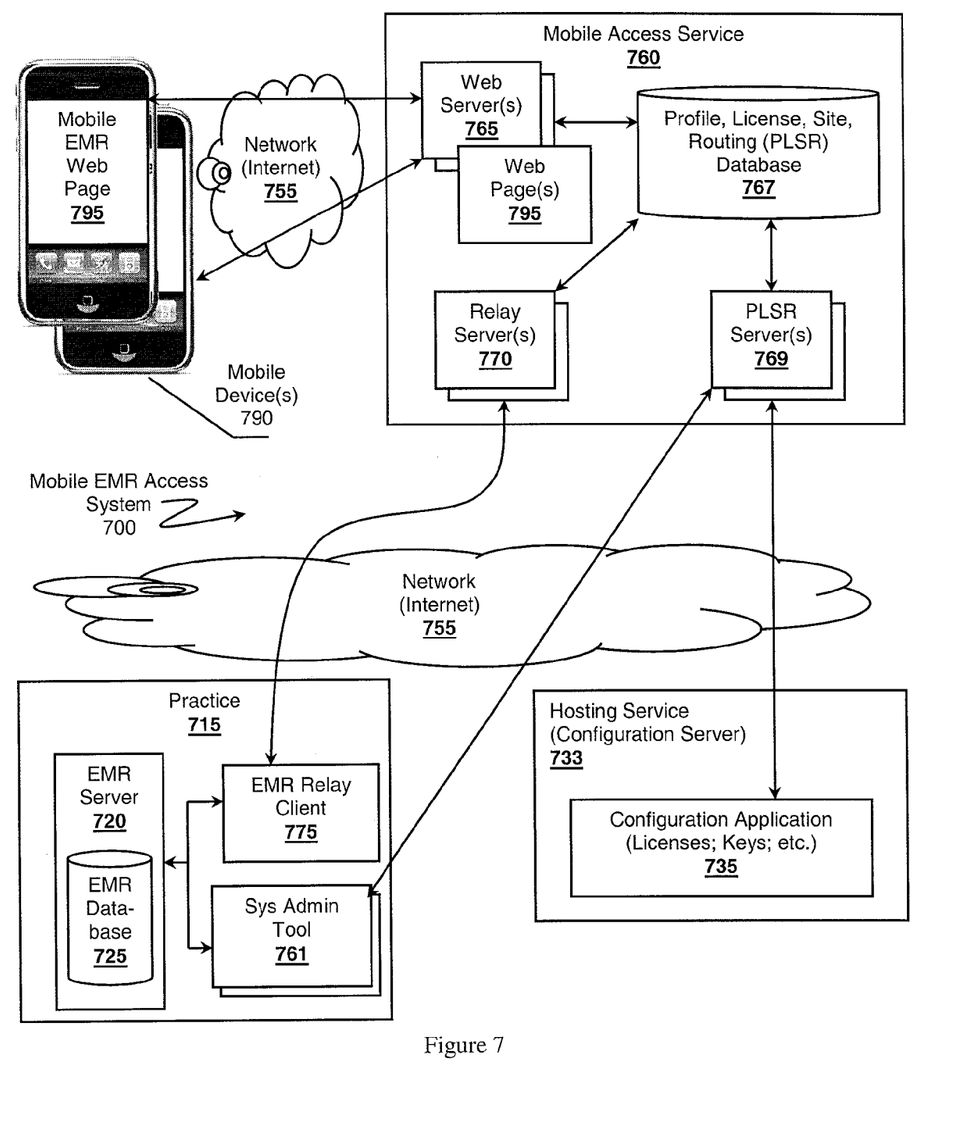
FIG. 7 provides an overview of a new practice integrating into an EMR distribution system.

FIG. 7 illustrates mobile EMR access system 700 where practice 715 represents a new subscriber of the services provided by mobile access service 760. Hosting service 733 represents an entity configured to host or offer mobile access service 760 to subscribes over network 755. One suitable example of an entity capable of supporting hosting service 733 or mobile access service 760 includes NextGen® Healthcare (see URL www.nextgen.com). Example services offered by NextGen that could be adapted for use with the disclosed subject matter include NextGen® Patient Portal, NextGen® Practice Management, or NextGen$^{SM}$ Health Information Exchange. Typically the hosting service would also represent the same entity providing software for EMR server 720, EMR database 725, system administrator tool 761, or other aspects of the EMR distribution system.

Mobile access service 760 can include Profile, License, Site, and Routing (PLSR) database 767, which includes sufficient information regarding practice 715 to broker requests from one or more mobile devices 790 for EMR data stored in EMR database 725. Profile information is considered to include data relating to mobile device 790 or its user (e.g., registration information, security tokens, email addresses, phone numbers, user information, preferences, permissions, etc.) so that mobile access service 760 properly exchanges data with mobile devices 790. Licensing information represents data indicating that practice 715 or its members have a proper license to obtain access to the services provided by mobile access service 760. In some embodiments, relay client 775 and relay server 770 can exchange licensing information to validate practice 715 as being a proper licensee. Site information includes data instructing relay server 770 how to interact with practice 715. One should appreciate that each practice 715 would likely have different site-wide preferences or configurations. Routing information includes data for use by mobile access service 760 for routing requests from mobile devices 790 through appropriate web servers 765 and over one or more data channels within the persistent sessions maintained by relay client 775 and relay server 770. As mobile devices 790 interact with web servers 765 to obtain EMR web pages 795, web servers 765 can consult PLSR database 767 to ensure the access should be permitted.

In a preferred embodiment, the burden on practice 715 can be dramatically reduced by allowing hosting service 733 configure the EMR application system at practice 715. Host service 733 can communicate with one or more PLSR server 767 to supply necessary configuration data to PSLR database 767. It some embodiments, each of practice 715 could have its own dedicated virtual PLSR server 767 configured to interface with system administrator tool 761. Such an approach aids in isolating one practice 715 from another, different practice 715 so that their private or proprietary data is not exposed to the other. Hosting service 733 can provide configuration application data 735 (e.g., license keys, site codes, etc.). Furthermore, practice 715 can use system administrator tool 761 to configure user or mobile device profile information.

Figure 8:
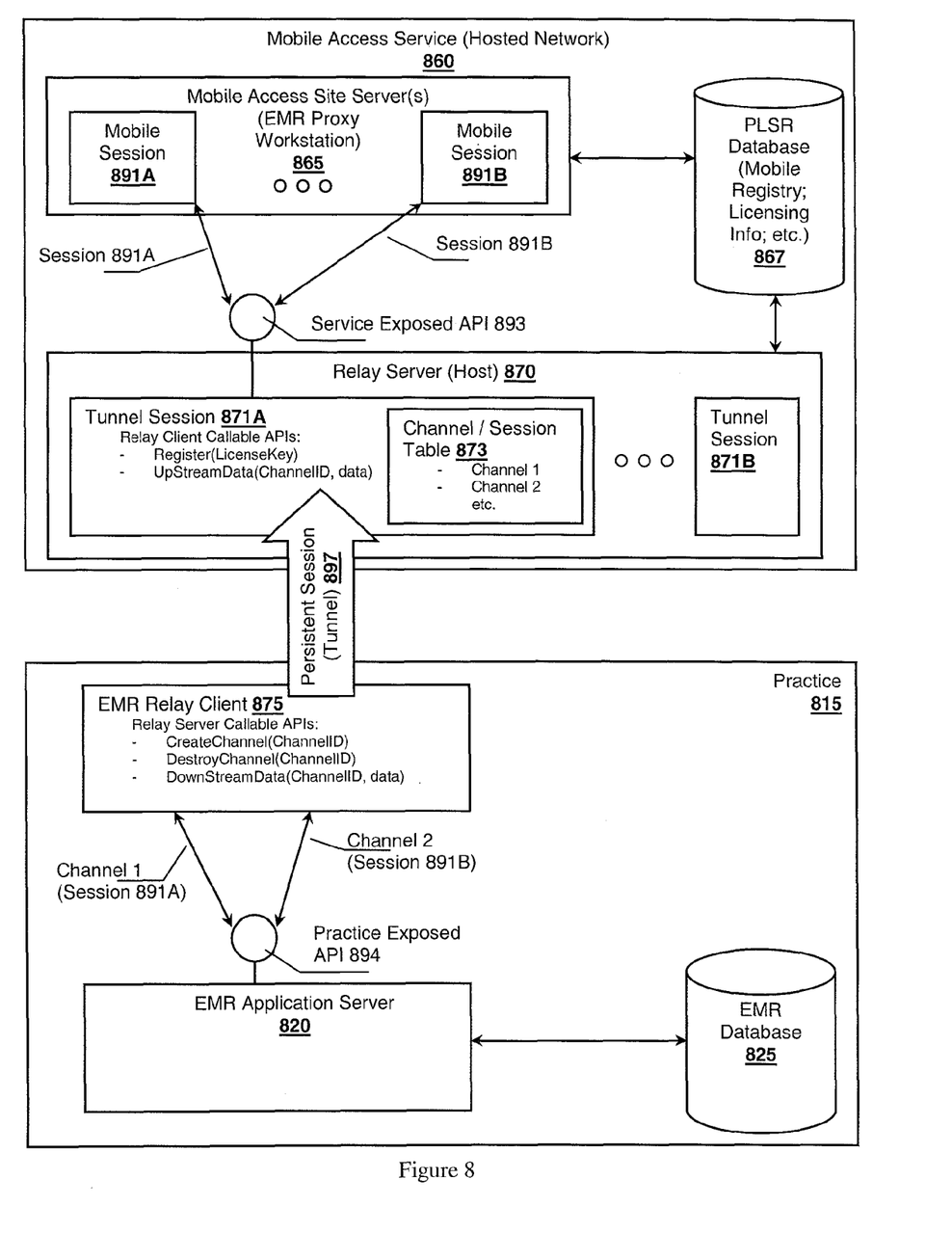
FIG. 8 presents a more detailed schematic of a possible embodiment for an EMR mobile access system.

FIG. 8 provides a more detailed view a possible architecture for establishing a persistent session between practice 815 and a mobile access service 860. Practice 815 establishes persistent session 897 with relay server 870 to allow remote mobile devices to access EMR data stored in EMR database 825.

When practice 815 installs relay client 875, relay client 875 can instantiate persistent session 897. Session 897 can include one or more data connections that form a data tunnel, through which mobile devices can gain access to EMR server 820. As discussed above, persistent session 897 preferably represents at least one initial outbound connection from relay client 875 to relay server 870. Persistent session 897 can include any supportable number of other connections including bi-directional channels, one or more inbound connections, or other types of connections.

Persistent session 897 can be constructed through the use of any desirable protocols for exchanging data between relay server 870 and relay client 875. More preferred embodiments utilize one or more TCP/IP connections, although connectionless channels could also be used as desired, possibly based on UDP/IP. Persistent session 897 operating as a data tunnel allows mobile EMR access servers 865 of the mobile access service 860 to operate similar to an EMR workstation application capable of communicating with EMR application server 820 at practice 815 even though the two sides of the EMR infrastructure can be separated by geographic distances over a network (e.g., the Internet). A the tunnel allows the mobile EMR access servers 865 to make calls to service exposed EMR APIs 893 as if the APIs were actually EMR APIs made available via EMR application server 820 as represented by practice exposed EMR APIs 894. Persistent session 897 provides the tunnel for data exchange between the two APIs: service exposed EMR APIs 893 and practice exposed EMR APIs 894.

When relay server 870 receives an initial connection request from relay client 875 for creating persistent session 897, relay server 870 can instantiate tunnel session 871A. One should note that relay server 870 could instantiate multiple tunnel sessions, tunnel session 871B for example, for a single practice 815 or for many different practices. Additionally, mobile access service 860 could have multiple relay servers 870, possibly a virtual server for each subscribing practice 815. Tunnel session 871A can be a dedicated to practice 815 once any proper authentication or authorization has been granted based on profile, licensing, site, routing, or registration information stored in PLSR database 867. For example, once tunnel session 871A has been established with at least one communication channel, relay client 875 can invoke a remote API Register ( ) located within tunnel session 871A. When invoked with a proper license key (e.g., tokens, site codes, etc.), relay server 870 can consult PLSR database 867 to determine if practice 815 is permitted to continue.

Tunnel session 871A can store one or more of mapping table 873 comprising a mapping between communication channels over persistent session 897 and mobile device sessions 891A through 891B. In some embodiment, tunnel session 871A or its individual channels can be secured using various security algorithms or protocols (e.g., AES, DES, 3DES, SSL, SSH, HTTPS, SHTTP, etc.).

When persistent session 897 is properly instantiated or otherwise established, remote mobile devices can begin to access EMR application server 820 by submitting queries to EMR database 825. One or more mobile devices direct their browser applications to mobile EMR access server 865, which provides an EMR workstation-like interface to the mobile devices, possibly in the form of a web page (e.g., HTML, scripts, Flash, etc.). Assuming the mobile devices or devices users are properly authenticated based on information in PLSR database 867, mobile EMR access server 865 can create one or more mobile session 891A through 891B. Multiple mobile sessions are illustrated to indicate practice 815 could have multiple active mobile devices, each with their own mobile session or that a single mobile device could have multiple mobile sessions.

Mobile EMR access site server 865 can be considered to operate as a EMR proxy workstation application where each mobile session 891A through 891B can be considered to comprise an independent EMR workstation interaction. Mobile sessions 891A through 891B can conduct EMR workstation-like interactions by access service exposed API 893 provided by relay server 870. For example, mobile session 891A can generate a query directed to EMR application server 820 just as an EMR workstation application would generate a query. In some embodiments, the generation of the query and calling of the API is substantially identical to how the EMR workstation local to practice 815 would conduct such actions. To make the query or other EMR request, mobile session 891A simply calls one or more of the service exposed API 893.

Upon receiving an EMR request via service exposed API 893, relay server 870 can instantiate one or more channels within tunnel session 871A for mobile sessions 891A through 891B. Relay server 870 uses mapping table 873 to track which of the instantiated channels are assigned to mobile sessions 891A through 891B. In some embodiments as shown, relay server 870 can instantiate a channel over persistent session 897 by invoking the remote API CreateChannel ( ) located on relay client 875. One should note that persistent session 897 can be considered a client-generated pending request for commands from relay server 870. When the channel is properly instantiated, relay server 870 and relay client 875 can exchange EMR request data.

EMR request data (e.g., commands, data, instructions, etc.) generated via mobile sessions 891A through 891B tunnels over the created channel within tunnel session 871A. When the EMR request data arrives as relay client 875, relay client 875 unpacks the EMR request data can call the corresponding practice exposed API 894. In response, EMR application server 820 can query or otherwise interact with EMR database 825 as instructed and return a result set back through practice exposed API 894 and on to mobile sessions 891A or 891B. Thus, relay server 870 and relay client 875 form a transparent tunnel between service exposed API 893 and practice exposed API 894 in a manner where mobile session 891A through 891B appear to interact directly with EMR application server 820, or vice versa.

It is also contemplated that relay server 870 and relay client 875 can provide channel management support to smooth communication issues that could arise. One management function could include providing a dummy response to issued EMR requests at service exposed API 893 to alleviate potential timing issues that could arise due to network latency persistent session 897, loss of connectivity, or other networking related issues. Yet another management function could include load balancing among more than one physical relay server machines.

The approached outlined with respect to FIG. 8 provides for ease of migration from existing practice-centric EMR application deployment to a mobile-based EMR application. Existing EMR applications, EMR server and EMR workstation applications, require little or no modifications. Relay client 875 can be installed quickly and easily by practice 815 to allow for mobile device access. Furthermore, EMR workstation/server applications can be easily integrated into the mobile infrastructure by the entity hosting mobile access service 860.

Figure 9:
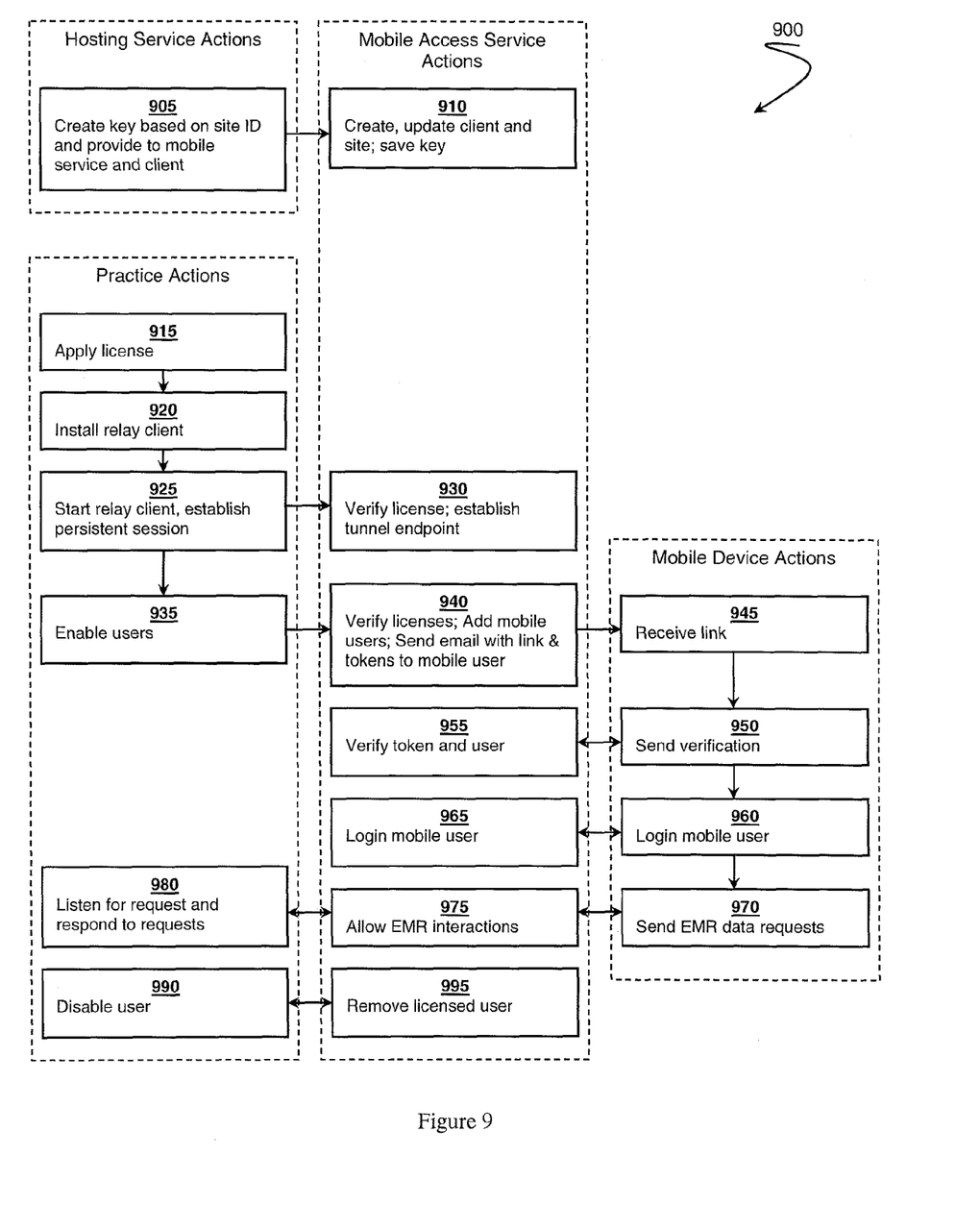
FIG. 9 illustrates a possible method for another possible embodiment of an EMR access system, which provides access via mobile access service having an EMR relay server.

FIG. 9 illustrates a possible method 900 for configuring an EMR distribution system that allows mobile devices to interact with an EMR database located at a practice. Windows Communication Foundation (WCF) framework can used to establish communication sessions, including the persistent session tunnel. Active Server Pages (ASP) can provide interface infrastructure to mobile devices. Naturally other types of software or networking infrastructure can be utilized to configure an EMR distribution system.

The example method 900 of FIG. 9 indicates which entity takes actions by dashed-line boxes surrounding the various steps of the methods. The dashed boxes represent the entity that can take the indicated actions, although all possible variations are contemplated without loss of scope with respect to the inventive subject matter.

At step 905 a hosting service can create one or more licensing keys based on a target practice's site identifier. Keys can take on any form and can include 32 bit, 64 bit, 128 bit, or even greater than 256 bit keys. In some embodiments a key can represent a hash of a site identifier (e.g., UUID, GUID, unique name, etc.) as desired. The key can be provided to the mobile access service once it is suitably generated.

At step 910 the mobile access service, possibly operated by the same entity as the hosting service, receives the key information and creates one or more client profiles for the practices and creates a mobile access site (e.g., web server, relay server, etc.) for the practice. Additionally, the mobile access service stores the licensing key or other information in a PLSR database for later retrieval.

At step 915 the practice can apply a license by entering a license key into an installed EMR application, possibly through a license manager application. Naturally, the hosting service can supply the license key to the practice through any suitable communications means including email, letter, CD key, keyfob, or other suitable methods. Typically applying the license can occur during an installation process of installing an EMR system at the practice.

At step 920, an individual or other entity associated with the practice can install a relay client local to the practice. The installed relay client, or other aspect of the EMR system, can utilize the license key information to ensure the practice is a valid licensee. Once installed, the relay client can be launched and can check for proper connectivity over a network with the mobile access service.

At step 925, the installed relay client can establish a persistent session by connecting with a relay service at the mobile access service. For example, the relay client can invoke a remote procedure call to a Register ( ) API within an established tunnel. The registration call can include license key or other validation information.

At step 930, the mobile access service executes the registration call and verifies the practice and relay client are indeed valid subscribes based on any provided licensing, site information, or any other practice information. The mobile access service can consult the PLSR database for confirmation of the information. Preferably up on verification of the practice's license information, the persistent session can be finalized by creating a tunnel endpoint within a server of the mobile access service. The relay client's action for establishing the persistent session can be considered submitting a pending request for commands or instructions to the relay server by causing the registration API to execute. Thus, the relay client waits or listens for an inbound EMR request.

At step 935, the practice can continue to configure their system by enabling users of mobile devices. A system administrator tool associated with the EMR applications can be used to provide or verify each user's email address or upload the user's profile information to the PLSR database resident within the mobile access service.

At step 940, the mobile access service receives the user information, or any associated licensing information, then verifies that practice's account information. Each user can be provided an individual license if desired for accounting or auditing purposes. The user profile information can be stored within the PSLR database for later retrieval to set preferences or for validation. Preferably the mobile access service generates a verification token that can be sent to the user's mobile device with an access link, possibly via Email or other messaging system, to allow the mobile device to register with or login to the mobile access service.

At step 945, the mobile device receives the access link and verification token. In some embodiments, the mobile device receives the access link via an email message. One should note that other forms of messaging can also be used to receive the links including SMS messages, HTTP, voice mail, or other messaging protocols.

At step 950, the mobile device user can access the link to cause the verification token to be sent back to the mobile access service. The mobile device can also generator one or more bookmarks within a browsing application of the mobile device to retain the login point for the mobile access service.

At step 955, the mobile access service receives the verification token and completes the mobile device registration process. The user of the mobile device can then be verified as a valid user of the mobile access service and as a valid user for gaining access to the EMR data located at the practice. One should note that the mobile device does not require any additional software other than pre-existing browser applications to interact with mobile access service. For example, the user can access one or more email accounts via the browser application. The provided links can be also encoded with security information.

At step 960, the user can begin an EMR session by logging into the mobile access service, possibly by selecting the bookmarked link. In response, at step 965, the mobile access service can login the user by verifying the user's information (e.g., email address, password, preferences, etc.) compared to the information in the PSLR database. If the user's information is indeed valid and authentication is successful, a mobile session can be created. At this point the user can utilize the mobile device to access their EMR data.

At step 970, the user can interact with an EMR interface (e.g., web page) provided by one or more servers of the mobile access service. Via the interface, the user can submit one or more EMR requests to the practice.

At step 975, the mobile access service allows the EMR interactions by receiving one or more instructions from the EMR interfaces and generates or otherwise packages the EMR request for tunneling through the persistent sessions between the practice's relay client and the service's relay server. At step 980, the practice's relay server listens for requests and responds, if possible. The practice can generate one or more result sets that satisfy the user's request. The results set can also be tunneled through the persistent session back to the relay server of the mobile access service, which in turn renders the result set for display on the mobile device. Through these interactions, the mobile device and practice can exchange EMR records.

One should note that the mobile access service is essentially operating as a proxy between the practice and the mobile device. Consequently, the mobile access service is not required to store or persistently maintain any EMR data records. In fact, in some embodiments, all EMR data is encrypted so that only the practice and mobile device endpoints can gain access to the data via decrypting the data records through an appropriate key. One should note that a encryption/decryption key could be used without requiring mobile access service being aware of the key. For example, the key could be defined at the practice by the user of the mobile device. Then the user can enter the same key at the mobile device to decrypt the information, assuming appropriate security modules are in place. Thus, the mobile access service would not be able to gain access to exchange EMR data. Furthermore, in some embodiments the servers of the mobile access service can be configured to stream EMR data result sets so that none of the EMR data is stored in a non-volatile memory (e.g., hard drive, solid state drive, flash, etc.).

At step 990, a practice can remove a mobile device user by removing account or profile information for the mobile device users. At step 995, the mobile access service can instruct the PSLR database to remove the necessary information for a user. More specifically, the user's or mobile device's tokens or licensing information can be removed. In some embodiments, other information relating to the mobile device can be retained. For example, the mobile access service can retain logs or auditing information that can be analyzed later for security or optimization purposes.

A number of embodiments have been presented above, each having their relative merits. It should be appreciated that features from each of embodiment could be combined with features of other embodiments as desired. For example, the embodiment represented in FIG. 6 might also incorporate the terminal server of FIG. 2.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of providing access to a plurality of Electronic Media Record (EMR) database, located within distinctive private networks of medical practices, the method comprising:
   enabling a mobile request device to generate an EMR request;
   providing access to a first EMR client corresponding to a first private network and a second EMR client corresponding to a second private network, each of the first and second private networks comprises an EMR database storing EMR data for a corresponding medical practice;
   providing a mobile access service located outside of the first and second private networks and capable of receiving the EMR request from the mobile request device via a wireless network;
   establishing, by each of the first and second EMR clients, a persistent session with the mobile access service via an outbound request; and
   receiving, at the mobile access service, an EMR request from a mobile device associated with an owner of the mobile device; p1 establishing, by the mobile access service, a first data channel with the first EMR client and a second data channel with the second EMR clients.
   generating a first query and second query that are distinct from each other, based on information derived from the EMR request;
   modifying the first and second data channels, by the mobile access service, based on the information derived from the EMR request and information associated with the mobile device and the owner
   automatically routing, by the mobile access service, the first query to the first EMR client and the second query to the second EMR client via the first and second data channels, respectively;
   obtaining, at the mobile access service, a first EMR result set from the first EMR client via the first data channels and a second EMR result from the second EMR client via the second data channel, the first and second result sets being products of running, by the first and second EMR clients the first and second queries in EMR databases of the first and second private network, respectively; and
   generating, by the mobile access service, a final result set based on the first and second result sets and sending the final EMR result to the mobile request device.

2. An Electronic Record (ER) distribution system, the system comprising:
   a plurality of ER databases corresponding to a plurality of distinct private networks of different organizations, each ER database storing data records for the corresponding organization and located within the corresponding private network of the organization;
   an ER client located within each of the private networks and configured to query the ER database for data records within the private network;

a mobile access service located outside of the plurality of private networks and configured to accept a ER request from a mobile device; and a remote request device enabled to exchange ER request information over a network with the mobile access service, and wherein each ER client establishes and maintains a persistent session with the mobile access service, and wherein the mobile access service is configured to establish a plurality of data channels with each ER client over the corresponding persistent session, to modify the data channels based on the ER request information and information associated with the mobile device, to generate at least two distinct ER request queries based on the received ER request information and route the ER request queries to at least two ER databases from among the plurality of ER databases via the data channels.

3. The system of claim 2, wherein the mobile access service comprises a channel manager configured to manage the persistent session by creating, removing, and modifying data channels between the ER client and the mobile access service.

4. The system of claim 3, wherein the channel manager is configured to modify the data channels based on a profile of the user and a profile of the mobile device.

5. The system of claim 4, wherein each of the plurality of channels is configured for use according to at least one of the following: record owner information, requester information, and license information.

6. The system of claim 5, wherein the record owner is a patient.

7. The system of claim 4, wherein the mobile request device is associated with a requester who is a member of a heath care practice.

* * * * *